United States Patent [19]

An et al.

[11] Patent Number: 5,590,206

[45] Date of Patent: Dec. 31, 1996

US005590206A

[54] NOISE CANCELER

[75] Inventors: Hyeong-keon An; Young-ho Shin; Suk-ki Kim, all of Kyungki-do, Rep. of Korea

[73] Assignee: Samsung Electronics Co., Ltd., Suwon, Rep. of Korea

[21] Appl. No.: 326,954

[22] Filed: Oct. 21, 1994

Related U.S. Application Data

[62] Division of Ser. No. 45,011, Apr. 9, 1993, Pat. No. 5,406, 149.

[30] Foreign Application Priority Data

Apr. 9, 1992 [KR] Rep. of Korea ........................ 92-5927

[51] Int. Cl.$^{6}$ ........................... H04B 29/00; H04B 15/00; A61F 11/06

[52] U.S. Cl. ................................................ 381/71; 381/94

[58] Field of Search .............................. 381/71, 94, 73.1, 381/86

[56] References Cited

U.S. PATENT DOCUMENTS

| | | | |
|---|---|---|---|
| H1,357 | 9/1994 | Ng et al. | 381/71 |
| 3,979,683 | 9/1976 | Ikeda . | |
| 4,153,815 | 5/1979 | Chaplin et al. | 381/71 |
| 4,268,793 | 6/1981 | Amazawa et al. . | |
| 4,654,871 | 3/1987 | Chaplin et al. | 381/71 |
| 4,701,715 | 10/1987 | Amazawa et al. . | |
| 4,924,121 | 5/1990 | Ohno . | |
| 5,022,082 | 6/1991 | Eriksson et al. | 381/71 |
| 5,109,533 | 4/1992 | Mine et al. . | |
| 5,182,478 | 1/1993 | Nomura . | |
| 5,267,310 | 11/1993 | Yoshiba | 381/71 |

*Primary Examiner*—Curtis Kuntz
*Assistant Examiner*—Xu Mei
*Attorney, Agent, or Firm*—Cushman Darby & Cushman, IP Group of Pillsbury Madison & Sutro LLP

[57] ABSTRACT

In a noise canceler, a pilot-canceling signal without noise is applied to the inverting input of a subtracter via a first MOS transistor. When a noise signal is present, a pilot signal and noise signal passing through a capacitor are applied to the inverting input port of the subtracter via a second MOS transistor to cancel the noise signal contained in the composite input signal. In the canceler, external noise may be digitally converted and the inverted noise thereof stored in a memory. When a noise signal detector detects the external noise, inverted data corresponding to the external noise is output from the memory. The detector enables an address generator to continuously generate addresses. The memory reads out inverted noise patterns which are converted into analog form and transmitted via a speaker, thereby canceling noises produced by various electrical and electronic appliances as well as nearby automobiles and aircraft.

4 Claims, 3 Drawing Sheets

NOISE CANCELER

This is a division of application Ser. No. 08/045,011, filed Apr. 9, 1993, now U.S. Pat. No. 5,406,149.

BACKGROUND OF THE INVENTION

The present invention relates to a noise canceler.

All electrical and electronic appliances use electricity represented by voltage and current. The flow of current through wire creates a magnetic field around the wire. Whenever a potential difference exists, electric and electromagnetic fields are produced in the surrounding space that vary over time. Also, when an AC voltage drop occurs, the supply voltage to a circuit is varied, which can cause the circuit to misoperate. Furthermore, these appliances generate electromagnetic waves which may impede the operation of other appliances or may cause their misoperation. Especially, noise produced during the starting of an automobile or the overhead passage of aircraft can result in the interruption of the normal operation of appliances.

FIG. 1 shows a conventional noise canceler that comprises a subtracter 1 having: a non-inverting input port (+) and an inverting input port (–); a subtracting signal $IN_2$ entering via the inverting input port; a signal $IN_1$ entering via the non-inverting input port; a signal OUT of which noise is canceled; and a capacitor C connected between the two input ports of subtracter 1.

A composite signal $IN_1$ input via the non-inverting input port of subtracter 1 is composed of a low frequency signal and pilot signal. The signal input via the inverting input port is a pilot canceling signal which has the same amplitude and phase as those of the pilot signal of the composite signal.

Subtracter 1 receives the composite signal via the non-inverting input port (+) and the pilot canceling signal via the inverting port (–) so as to output the difference. The difference signal voltage is equal to the voltage applied to either terminal of capacitor C connected between the non-inverting input port and inverting input port of subtracter 1.

Capacitor C blocks low frequency components and transmits high frequency components only. When the composite signal is applied to the inverting input port of subtracter 1, the low frequency signal is output through the output port of subtracter 1. If a noise signal is also present in the composit input signal $IN_1$, the input waveform of the non-inverting input port of the subtracter 1 is the same as that of the inverting input port. This is because the input impedance of subtracter 1 is extremely high. Capacitor C, acting as a filter, is effectively an AC short so that, when a noise signal is contained in the composite signal $IN_1$, the noise signal is simultaneously applied to the non-inverting input port and inverting input port of subtracter 1. According to these operations, the noise signal is not passed to the output port of subtracter 1 and the subtracter output is the voltage difference between the direct current components of the non-inverting input port and inverting input port.

However, in this configuration, the pilot signal and the noise signal of the composite input $IN_1$ pass through capacitor C and interfere with the pilot canceling signal applied to the inverting input port of subtracter 1. Performance of the noise canceler is thus reduced.

SUMMARY OF THE INVENTION

Therefore, it is an object of the present invention to provide an analog noise canceler having improved signal processing performance by, normally applying only a pilot canceling signal through the non-inverting input port of a subtracter. When noise is produced, a signal output from a capacitor is applied.

It is another object of the present invention to provide a digital noise canceler for canceling noise by storing data inverted with respect to various normalized noise signals in a memory and reading them out from the memory when a corresponding noise signal is detected.

BRIEF DESCRIPTION OF THE DRAWINGS

The above objects and other advantages of the present invention will become more apparent by describing in detail a preferred embodiment thereof with reference to the attached drawings in which.

FIGS. **5*a* and 5*b* are block diagrams of digital noise cancelers according to the present invention.

DETAILED DESCRIPTION OF THE INVENTION

Figure 1:
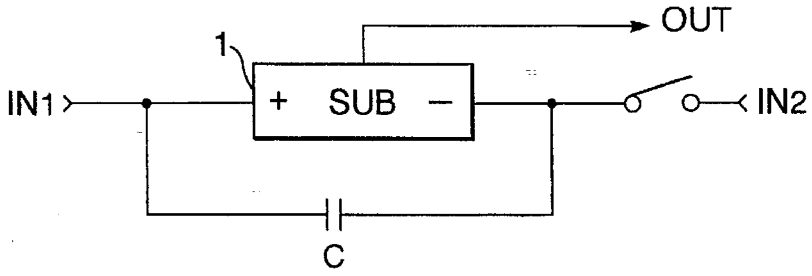
FIG. 1 (PRIOR ART)
FIG. 1 is a block diagram of a conventional noise canceler.
Figure 2:
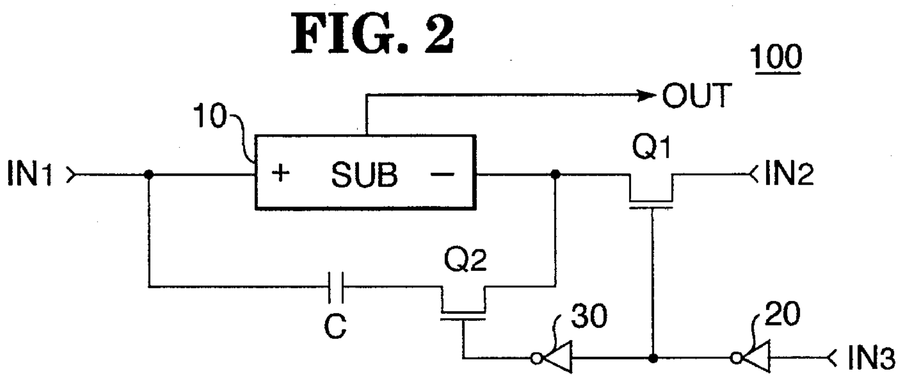
FIG. 2 is a block diagram of an analog noise canceler according to the present invention.

In FIG. 2, reference numeral 10 represents a subtracter, and reference numerals 20 and 30 represent inverters. Further, reference characters $Q_1$ and $Q_2$ indicate NMOS transistors and character C indicates a capacitor.

In FIG. 2, the noise canceler 100 of the present invention comprises a subtracter 10 having a non-inverting input port (+) and an inverting input port (–) used for subtracting first and second input signals $IN_1$ and $IN_2$ and outputting an output signal (OUT). A transmission transistor $Q_1$ connected to the inverting input port of subtracter 10 controls the input of the second input signal. A capacitor C and transmission transistor $Q_2$ connected in series between the non-inverting input port and inverting input port of subtracter 10 control input of a noise signal (derived from $IN_1$) into the inverting input port. Inverters 20, 30 inverting a third input signal $IN_3$ so that the inverted input signal $IN_3$ controls transmission transistor $Q_1$, and so that the non-inverted input signal $IN_3$ controls transmission transistor $Q_2$.

A composite signal input via the non-inverting input port of subtracter 10 consists of a low frequency signal and pilot signal. A pilot canceling signal input via the non-inverting input port of subtracter 10 has the same amplitude and phase as those of the pilot signal contained in the composite signal. The composite signal, which normally does not include a noise signal, is applied to the non-inverting input port of subtracter 10. At this time, the pilot canceling signal is applied to the inverting input port of subtracter 10.

When a noise signal is present, the composite signal is composed of the low frequency signal, pilot signal and noise signal and is applied to the non-inverting input port of subtracter 10. Here, a filtered derivative of the composite signal that has passed through capacitor C is applied to the inverting input port of subtracter 10. Input signal $IN_3$ determines which signal is applied as the pilot canceling signal: either the input signal $IN_2$ passing through transistor $Q_1$ or the signal passing through capacitor C and transistor $Q_2$.

Figure 3:
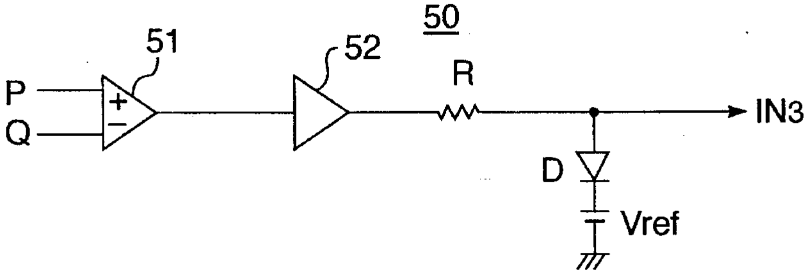
FIG. 3 is a circuit diagram for generating the signal applied to the circuit of FIG. 2.

FIG. 3 shows a circuit diagram for producing input signal $IN_3$ illustrated in FIG. 2. Here, reference numeral 50 denotes a control signal generating circuit, reference numeral 51 indicates a comparator, reference numeral 52 indicates an amplifier, the letter R indicates a resistor, D denotes a diode, and $V_{ref}$ indicates a reference voltage source.

The circuit of FIG. 3 comprises a comparator 51 having a non-inverting input port (+) for receiving a signal P, an inverting port (–) for receiving a signal Q, an amplifier 52 for receiving and amplifying the output signal of comparator 51, a resistor R connected between the output of amplifier 52 and the output port of the control signal generating circuit, a diode D whose anode is also connected to the output port of the control signal generating circuit, and a reference voltage source $V_{ref}$ connected between the cathode of diode D and ground.

Comparator 51 receives a mixed signal containing a pilot signal and a noise signal after having passed through capacitor C, (in which the low frequency signal of the composite signal has been removed) via its non-inverting input port, and receives the pilot canceling signal via its inverting input port. Amplifier 52 is connected to comparator 51 so as to amplify the signal output from the comparator 51 to a predetermined level. Diode D and reference voltage source $V_{ref}$ maintain predetermined levels for output signal $IN_3$ so as to control the transistors $Q_1$ and $Q_2$. For instance, if reference voltage source $V_{ref}$ is 4.3 V, the voltage applied to the anode of diode D must exceed 5 V to turn on diode D (because the forward voltage for diode D is 0.7 V). Accordingly, when diode D is turned on, the voltage across the series configuration of diode D and reference voltage source $V_{ref}$ become 5 V.

Figure 4A:
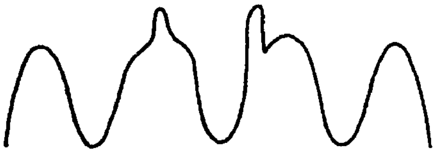
FIGS. 4A–4D are operating timing diagrams for illustrating the operation of the circuit shown in FIG. 3.
Figure 4B:
Figure 4C:
Figure 4D:

FIG. 4A shows the waveform of a mixed signal applied to the non-inverting input port of comparator 51. FIG. 4B is the waveform of the mixed signal applied to the inverting input port of comparator 51. FIG. 4C is the waveform of the output signal of comparator 51. FIG. 4D is the waveform of output signal $IN_3$ of the control signal generating circuit 50.

In FIG. 3, comparator 51 receives the mixed signal shown in FIG. 4A through its non-inverting input port and receives the pilot canceling signal shown in FIG. 4B through its inverting input port, so as to generate a high-level output signal when noise is present and to generate a low-level output otherwise. The signal generated from comparator 51 is illustrated in FIG. 4C. Amplifier 52 connected to the output of comparator 51 amplifies the output signal of comparator 51 to a predetermined level which is thereafter kept at a predetermined level, e.g., +5 V, by the series-connected diode D and reference voltage source $V_{ref}$. As a result, the output signal of the control signal generating circuit, i.e., input signal $IN_3$, has the same waveform as that of FIG. 4D and is used as a control signal of noise canceler 100 shown in FIG. 2.

When input signal $IN_3$ from the control signal generating circuit is "LOW" (when no noise signal is present), the pilot canceling signal $IN_2$ is switched to the inverting input port of subtracter 10. This is because signal $IN_3$ is inverted by first inverter 20 of FIG. 2 so as to apply a "HIGH" to the gate electrode of transmission transistor $Q_1$ connected to the inverting input port of subtracter 10. Thus, transmission transistor $Q_1$ is turned on and transmits the pilot canceling signal. Subtracter 10 receives the composite signal via its non-inverting input port and receives the pilot canceling signal having passed through transmission transistor $Q_1$, via its inverting input port, so as to subtract the two signals. The subtracted result is transmitted as output signal OUT via the output port. Since the composite signal usually consists of a low frequency signal and pilot signal and the pilot canceling signal has the same amplitude and phase as those of the pilot signal, the output signal OUT of subtracter 10 becomes the low frequency signal.

Conversely, when signal $IN_3$ from the control signal generating circuit 50 is "HIGH" (when a noise signal is present), the signal passing through capacitor C is applied to the inverting input port of subtracter 10. The control signal $IN_3$ is inverted by the first inverter 20 (now "LOW") is applied to and thus turns off transmission transistor $Q_1$ and the signal inverted by the second inverter 30 (now "HIGH") is applied to transmission transistor $Q_2$ so as to turn it on. Thus, a derivative of the composite signal is applied to the inverting input of the subtractor 10. Here, capacitor C blocks the low frequency signal of the composite signal and transmits the remaining signals, that is, the pilot signal and noise signal. The pilot signal and noise signal are applied to the inverting input port of subtracter 10. Therefore, the low frequency signal again is output from subtracter 10, so that the noise signal contained in the composite signal is reduced.

FIGS. *5a* and *5b* are block diagrams of digital noise signal cancelers according to the present invention.

In FIG. *5a*, when a noise signal is input via microphone 310, noise signal detector 320 detects the noise signal. Address generator 330 iS connected to the output of noise signal detector 320 so as to be enabled by the output signal of noise signal detector 320 and to determine a starting address of ROM 340. Then, address generator 330 sequentially counts up by ones. ROM 340 reads out inverted noise data according to the address generated by address generator 330. When the data read out from ROM 340 is applied to D/A converter 350, the D/A converter converts the data into analog form to be sent to amplifier 360. The signal from amplifier 360 is output through speaker 370. The sound from the speaker 370 cancels the noise.

In an alternate arrangement, the inverted noise can be added electronically as shown in FIG. *5b*. When a sound plus noise is received by the microphone 310, inverted noise is regenerated from memory as described above. However, rather than using a speaker to produce actual sound waves, an adder 330 adds the signal-plus-noise (from the microphone 310) to the inverted noise. By doing this, the noise signal is canceled.

Figure 6:
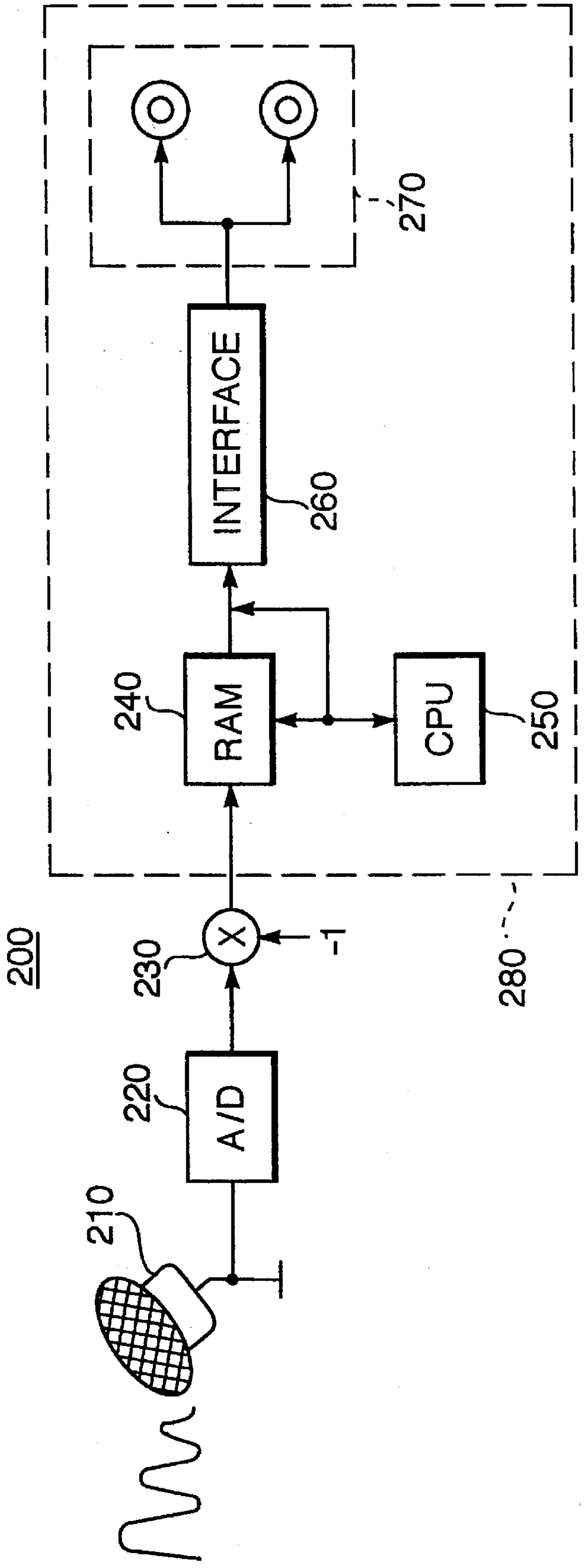
FIG. 6 is a block diagram of a system for recording inverted noise data stored in a memory of digital noise cancelers shown in FIGS. 5*a* and 5*b***.

FIG. 6 illustrates a block diagram of a system for recording inverted noise signals stored in a memory of a digital noise signal canceler according to the present invention.

In FIG. 6, a normalized specific noise signal is input via a microphone 210. The signal passing through microphone 210 is transmitted to an A/D converter 220 which samples and quantizes the received signal and divides the quantized signal into predetermined number of classes so as to encode them. For instance, if the quantized signal is divided into eight classes, the number of bits required for encoding is three, and if the signal is divided into sixteen classes, four bits are required for the encoding. Thus, A/D converter 220 continues to generate data having a predetermined number of bits and sends the converted data to multiplier 230. Multiplier 230 multiplies the data output from A/D converter 220 by −1 and transmits the result to a personal computer 280. For instance, given the data of A/D converter 220 is a binary four (0100), the output data from multiplier 230 is –4.

One way to obtain negative data is to take the 2's complement thereof. In this method, after the complement of 1 is found for the data, the result is added to "1". This can be expressed as follows:

```
 0100  .... data
 1011  .... complement of 1
+   1
1100   .... data of negative
```

Figure 5A:
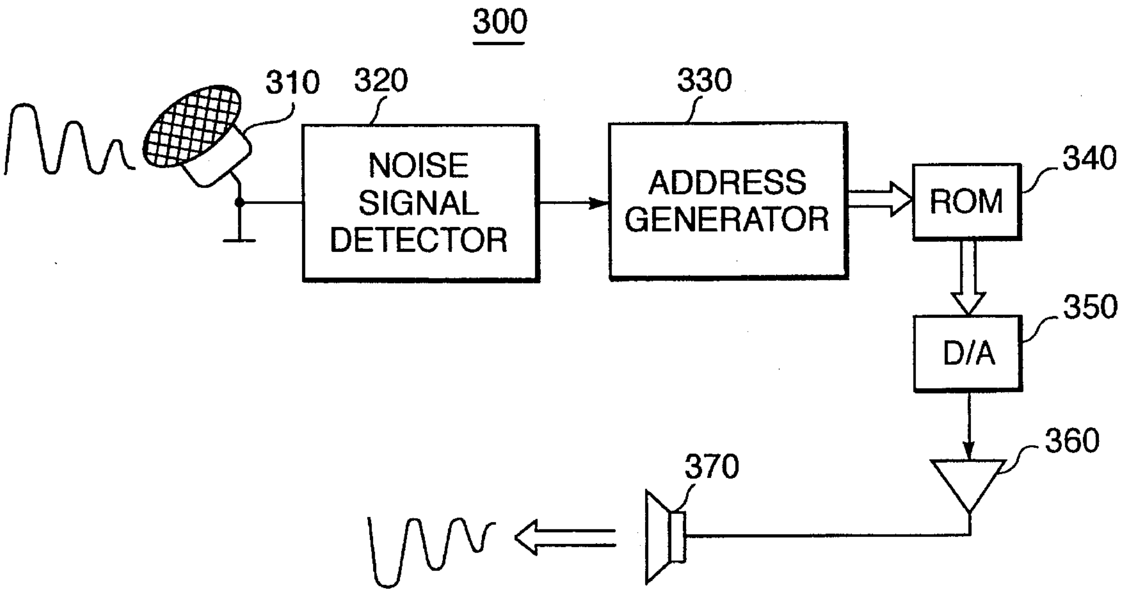
Figure 5B:
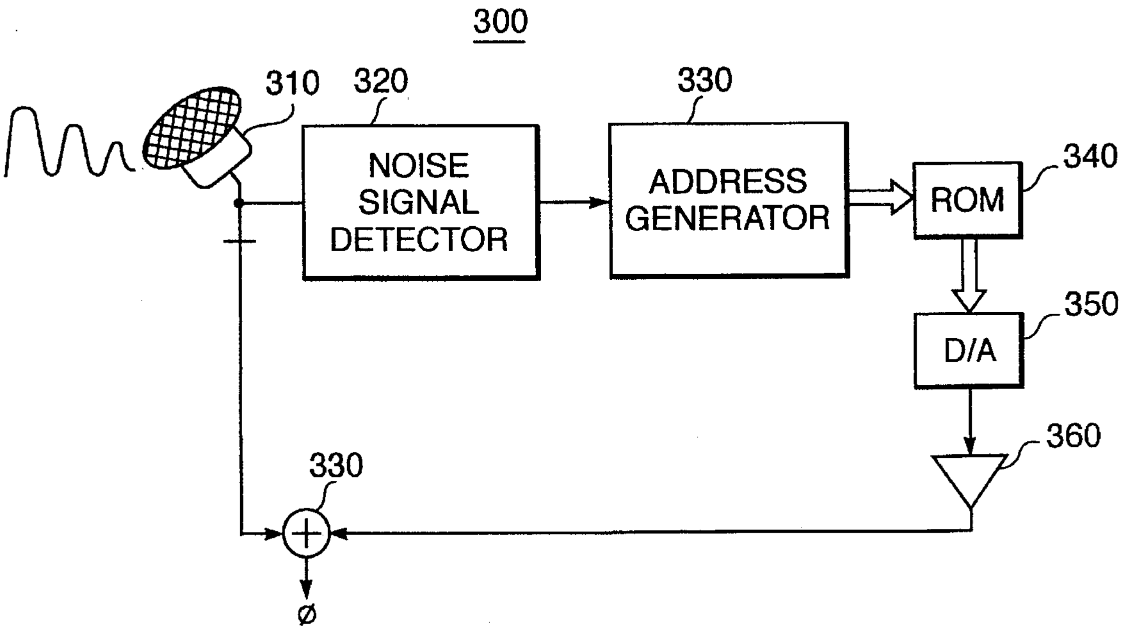

Under the control of CPU 250 of personal computer system 280, RAM 240 temporarily stores the output data of multiplier 230 and then stores them in an auxiliary storage 270 via an interface 260. (The media used for auxiliary storage 270 is ordinarily tape or disk.) The necessary noise patterns from the data stored in auxiliary storage 270 can be programmed in a later-mentioned ROM 340 of FIGS. 5*a* and 5*b*.

In other words, FIG. 6 illustrates a noise signal converter and recording system for encoding various noise signal and storing the inverted noise data thereof in a memory, using a personal computer.

Accordingly, the noise canceler of the present invention is useful to cancel the noises created in electrical or electronic appliances or, noises which may emanate from other appliances or from the engines of automobiles or overhead aircraft.

What is claimed is:

1. A noise canceler, comprising:

a noise detector;

an address sequencer connected to the noise detector;

a memory connected to the address sequencer, said memory storing predetermined inverted digitized noise patterns and regenerating the predetermined inverted digitized noise patterns in response to the address sequencer;

a D/A converter receiving said predetermined inverted digitized noise patterns from the memory and converting said predetermined inverted digitized noise patterns into analog form;

a speaker connected to the D/A converter and generating inverse noise signals.

2. The noise canceler of claim 1, wherein said memory comprises:

an A/D converter for receiving, sampling and quantizing a normalized specific noise signal, means for dividing the quantized signal into a predetermined number of classes to encode the divided signal;

an inverter receiving the output data from the A/D converter and generating inverted noise patterns; and a memory storing said predetermined inverted noise data.

3. A noise canceler as claimed in claim 2, wherein said memory storing said predetermined inverted noise patterns is composed of a personal computer system.

4. A noise canceler, comprising:

a noise detector;

an address sequencer connected to the noise detector;

a memory connected to the address sequencer, said memory storing predetermined inverted digitized noise patterns and regenerating the predetermined inverted digitized noise patterns in response to the address sequencer;

a D/A converter receiving said predetermined inverted digitized noise patterns from the memory and converting said predetermined inverted digitized noise patterns into analog form;

an adder combining analog-form inverted noise patterns from the D/A converter with a mixed signal-plus-noise and generating a reduced noise signal.

* * * * *